(12) United States Patent
Greeley et al.

(10) Patent No.: US 11,717,373 B2
(45) Date of Patent: Aug. 8, 2023

(54) ILLUMINATED ELECTROSURGICAL DEVICES, SYSTEMS AND METHODS

(71) Applicant: Medtronic Advanced Energy LLC, Minneapolis, MN (US)

(72) Inventors: Roger Greeley, Portsmouth, NH (US); Peter Goodwin, Portsmouth, NH (US); John Gearheart, Dover, NH (US); Ethan Carter, Epping, NH (US); Kevin McElwee, Berwick, ME (US); Jonathan Barry, Rochester, NH (US)

(73) Assignee: MEDTRONIC ADVANCED ENERGY LLC, Minneapolis, MN (US)

( * ) Notice: Subject to any disclaimer, the term of this patent is extended or adjusted under 35 U.S.C. 154(b) by 1226 days.

(21) Appl. No.: 16/264,208

(22) Filed: Jan. 31, 2019

(65) Prior Publication Data
US 2019/0380805 A1 Dec. 19, 2019

Related U.S. Application Data

(60) Provisional application No. 62/686,985, filed on Jun. 19, 2018.

(51) Int. Cl.
*A61B 90/30* (2016.01)
*A61B 18/14* (2006.01)
(Continued)

(52) U.S. Cl.
CPC .......... *A61B 90/30* (2016.02); *A61B 18/1402* (2013.01); *A61B 90/36* (2016.02);
(Continued)

(58) Field of Classification Search
CPC ......... A61B 90/30; A61B 90/35; A61B 90/36; A61B 2090/306; A61B 2090/308;
(Continued)

(56) References Cited

U.S. PATENT DOCUMENTS

| 7,736,361 B2 | 6/2010 | Palanker et al. |
| 2005/0063177 A1* | 3/2005 | Correa ..................... B25B 9/02 |
| | | 362/109 |

(Continued)

FOREIGN PATENT DOCUMENTS

| CN | 201743764 | 2/2011 |
| EP | 2767217 | 8/2014 |
| WO | WO 2006/043195 | 4/2006 |

OTHER PUBLICATIONS

International Search Report and Written Opinion from PCT Application PCT/US2019/016085 dated Apr. 24, 2019, 12 pgs.
(Continued)

*Primary Examiner* — Ronald Hupczey, Jr.
*Assistant Examiner* — Bradford C. Blaise
(74) *Attorney, Agent, or Firm* — Patterson Thuente, P.A.

(57) ABSTRACT

Embodiments relate to illuminated electrosurgical devices and related systems and methods. An electrosurgical device can include an electrosurgical blade having a proximal end and a distal end and comprising a plurality of light elements. A plurality of separation walls and a plurality of apertures can be arranged relative to the plurality of light elements to guide light from the plurality of light elements to illuminate an area around the distal end of the electrosurgical blade.

32 Claims, 17 Drawing Sheets

(51) Int. Cl.
    *A61B 18/00*     (2006.01)
    *A61B 18/02*     (2006.01)
    *A61B 90/00*     (2016.01)

(52) U.S. Cl.
    CPC ............ *A61B 2018/0091* (2013.01); *A61B 2018/00178* (2013.01); *A61B 2018/00589* (2013.01); *A61B 2018/00601* (2013.01); *A61B 2018/00982* (2013.01); *A61B 2018/0231* (2013.01); *A61B 2018/1475* (2013.01); *A61B 2090/309* (2016.02)

(58) Field of Classification Search
    CPC .... A61B 2090/309; A61B 2018/00178; A61B 2018/00196; A61B 2018/0091; A61B 2018/00982; A61B 2018/0231; A61B 2018/1475; A61B 18/14; A61B 18/1402
    See application file for complete search history.

(56) References Cited

U.S. PATENT DOCUMENTS

| | | | | |
|---|---|---|---|---|
| 2008/0045802 | A1* | 2/2008 | Brandstaetter | A61B 1/0684 600/199 |
| 2012/0221000 | A1 | 8/2012 | Bromley et al. | |
| 2013/0101953 | A1* | 4/2013 | Stone | F21V 5/04 433/29 |
| 2014/0005555 | A1 | 1/2014 | Tesar | |
| 2014/0293590 | A1* | 10/2014 | Pathy | F21L 4/02 362/184 |
| 2015/0049467 | A1* | 2/2015 | Thompson | B25B 15/02 362/120 |
| 2015/0209100 | A1* | 7/2015 | Ineson | A61B 18/1402 606/42 |
| 2015/0359581 | A1* | 12/2015 | Albertal | A61B 18/14 606/49 |
| 2016/0120592 | A1 | 5/2016 | Sylvester et al. | |
| 2016/0157920 | A1 | 6/2016 | Vayser et al. | |
| 2017/0143199 | A1* | 5/2017 | Grimmer | A61B 1/0676 |
| 2017/0172646 | A1 | 6/2017 | Patel et al. | |
| 2017/0258550 | A1* | 9/2017 | Vazales | A61B 90/70 |
| 2019/0321093 | A1 | 10/2019 | Greeley et al. | |

OTHER PUBLICATIONS

International Preliminary Report on Patentability from PCT Application PCT/US2019/016085 dated Dec. 30, 2020, 7 pgs.

* cited by examiner

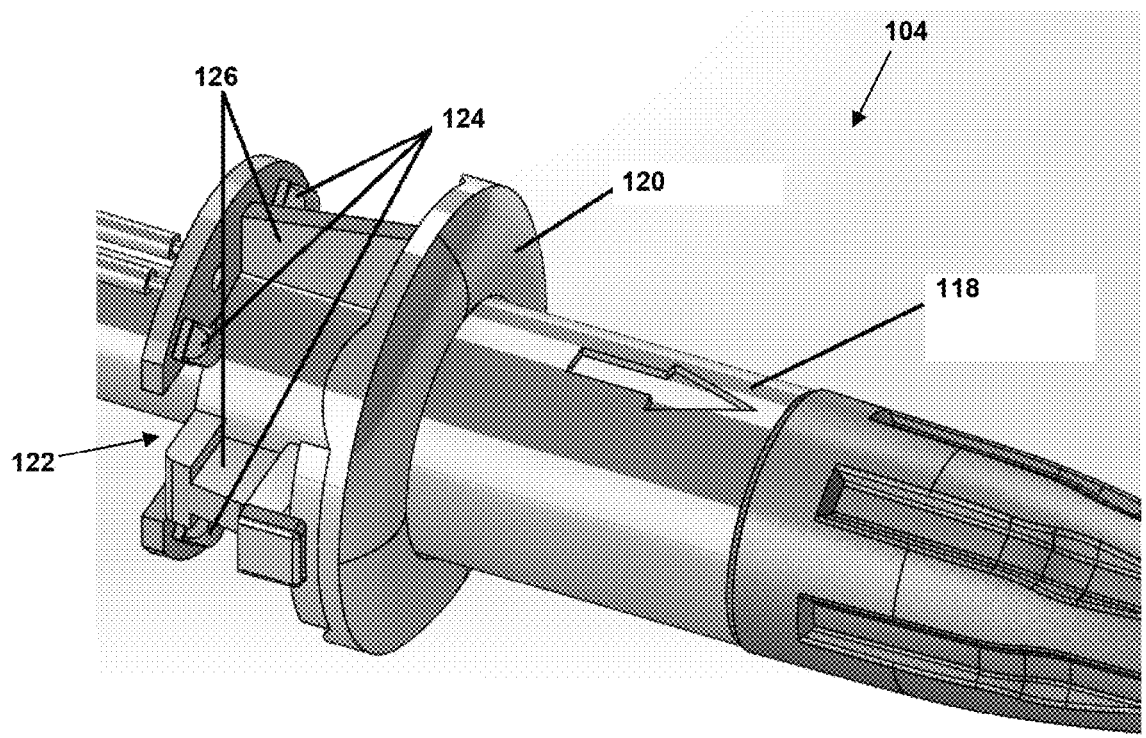
FIG. 2A
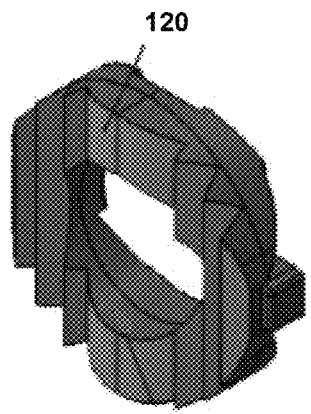 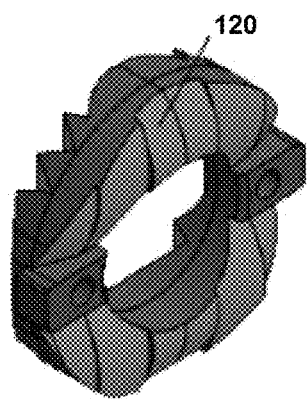
FIG. 2B  FIG. 2C

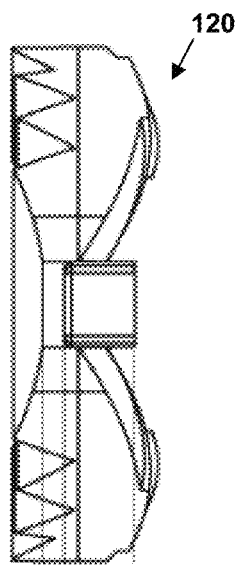
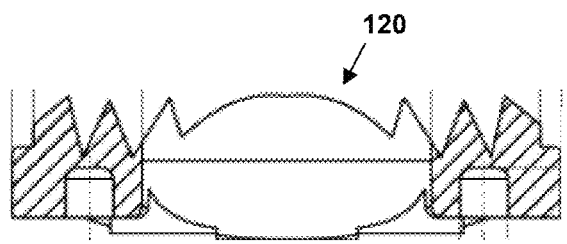
FIG. 2D    FIG. 2E
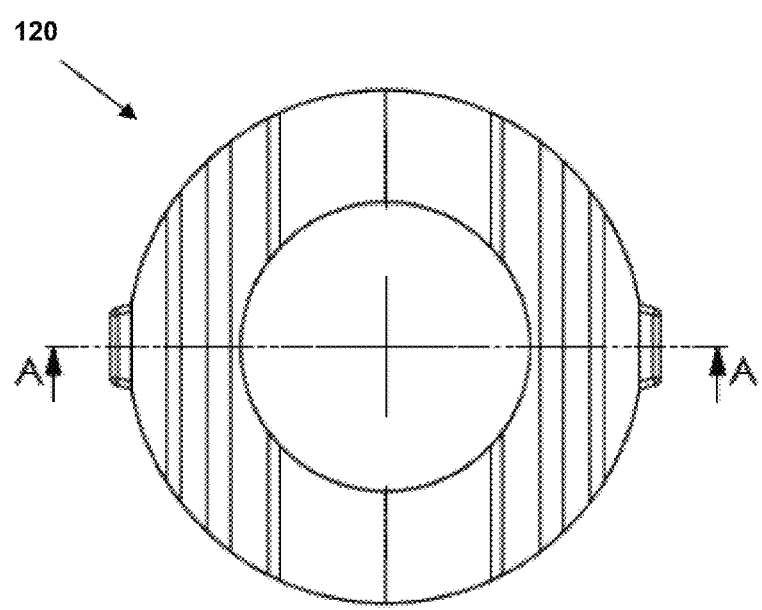
FIG. 2F

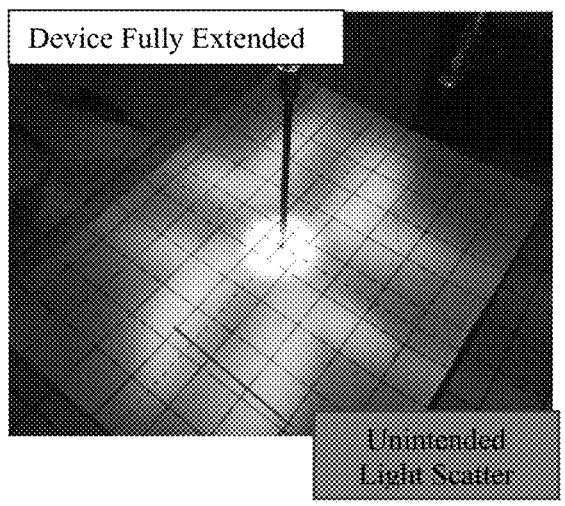 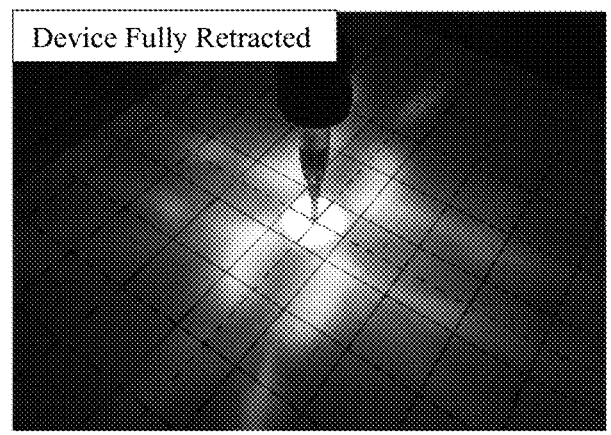
FIG. 8A                    FIG. 8B

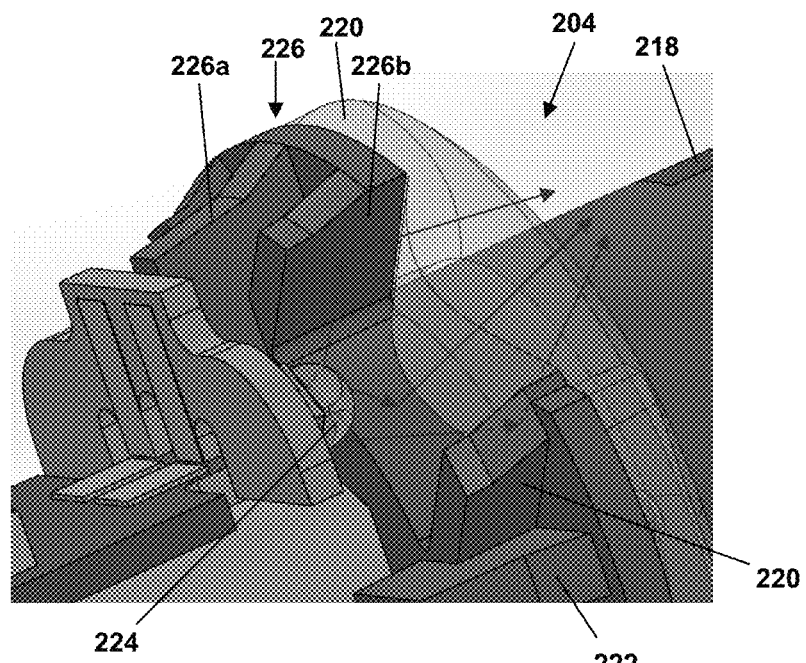
FIG. 11B
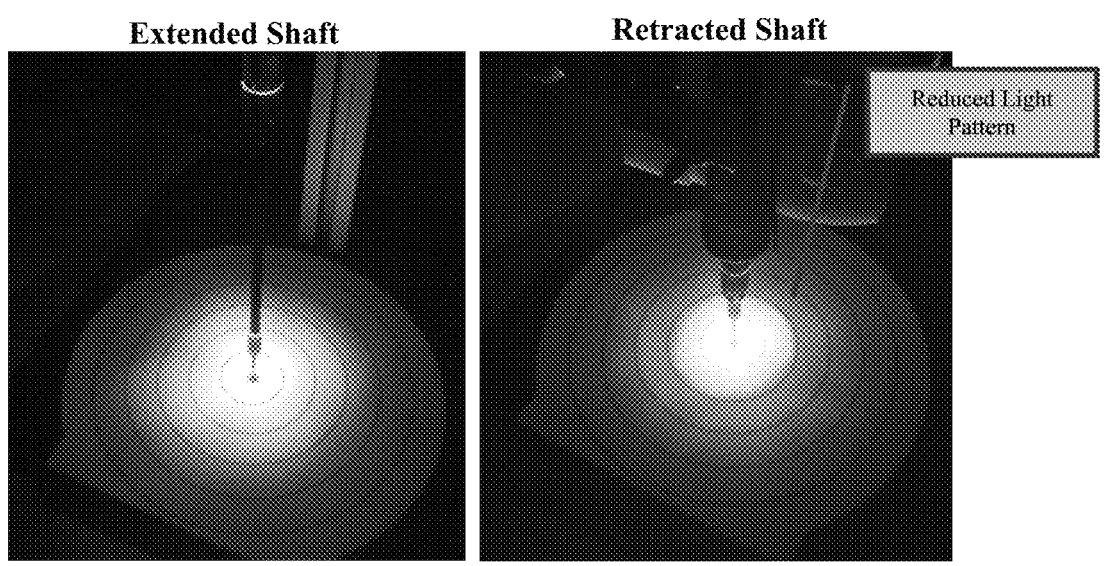
FIG. 12A  FIG. 12B

ILLUMINATED ELECTROSURGICAL DEVICES, SYSTEMS AND METHODS

RELATED APPLICATION

This application claims the benefit of U.S. Provisional Application No. 62/686,985 filed on Jun. 19, 2018, the entirety of which is incorporated herein by reference.

TECHNICAL FIELD

This disclosure relates generally to electrosurgical devices and more particularly to electrosurgical devices with integrated illumination systems.

BACKGROUND

Electrosurgical devices generally include a handpiece (handle) ergonomically adapted for ease of manipulation by a surgeon during surgery, and for positioning an energy tip of the device to deliver electrical energy to a target tissue for tissue cutting or coagulation. An electrode and electrical supply cable are generally disposed within the handpiece, traversing from the handpiece's proximal end through the handpiece body, and terminating in an energy discharge tip at the distal end of the device. The electrical supply cable typically is connected to an energy source, such as a radiofrequency (RF) energy generator.

The handpiece or other portion of the device may include an illumination element for illuminating the surgical field. This can be particularly helpful in situations in which a pocket is created inside of tissue, as overhead light or light from a headlamp cannot be directed easily into the pocket. Using an illuminated electrosurgical device, light may be conducted towards the energy discharge tip and directed onto the surgical field via an optical waveguide or lens coupled to the handpiece or disposed within the handpiece. The electrode may be disposed within the optical waveguide, or disposed alongside the waveguide. The electrode and waveguide may be disposed within a suitable supporting structure (for example, a cylindrical metal tube), that may be slidably extendable or retractable to permit the electrosurgical device to elongate or shorten as needed to treat the surgical site.

SUMMARY

Embodiments relate to illuminated electrosurgical devices and related systems and methods.

In one embodiment, an electrosurgical device comprises a central shaft; an electrosurgical blade coupled with the central shaft and comprising a tip; at least one lens element arranged around the central shaft and having a first side and a second side; and a plurality of light sources arranged around the central shaft to direct light to the first side of the at least one lens element; wherein the central shaft comprises a hub portion arranged around the central shaft and comprising a plurality of separation walls between the plurality of light sources and the first side of the at least one lens element, the plurality of separation walls spaced apart from one another around a circumference of the hub portion such that one of the plurality of light sources is between adjacent ones of the plurality of separation walls so that the adjacent ones of the plurality of separation walls guide light from the one of the plurality of light sources to the first side of the at least one lens element and therethrough toward the tip of the electrosurgical blade on the second side of the at least one lens element.

In another embodiment, a method comprises coupling an electrosurgical blade to a central shaft; arranging at least one lens around the central shaft; arranging a plurality of light sources around the central shaft on a first side of the at least one lens to direct light toward the first side of the at least one lens; and forming a hub portion around the central shaft on the first side of the at least one lens such that each one of a plurality of separation walls of the hub, spaced apart from one another around a circumference of the hub portion, is arranged between two adjacent ones of the plurality of light sources.

In yet another embodiment, an electrosurgical device comprises a ring lens having a circumference, a first side and a second side; a plurality of light sources arranged on a circuit board on the first side of the ring lens, spaced apart from one another along the circumference of the ring lens; and a plurality of separation walls each extending from the circuit board to the first side of the ring lens, one of the plurality of separation walls arranged between adjacent ones of the plurality of light sources to guide light from the one of the plurality of light sources to the first side of the rings lens and therethrough toward a tip of the electrosurgical device on the second side of the ring lens.

In a further embodiment, an electrosurgical device comprises a central shaft; an electrosurgical blade coupled with the central shaft and comprising a tip; at least one lens arranged on the central shaft and having a first side and a second side; a plurality of light sources arranged to direct light to the first side of the at least one lens; a plurality of separation walls each comprising a fin-like separation wall portion and two additional separation wall portions, the fin like separation wall portion arranged between the two additional separation wall portions, the plurality of separation walls arranged around the central shaft between the plurality of light sources and the first side of the at least one lens; and a plurality of apertures, wherein the plurality of separation walls are spaced apart from one another around a circumference of the central shaft such that one of the plurality of light sources and one of the plurality of apertures is between adjacent ones of the plurality of separation walls so that the adjacent ones of the plurality of separation walls and a respective one of the plurality of apertures guide light from a respective one of the plurality of light sources to the first side of the at least one lens and therethrough toward the tip of the electrosurgical blade on the second side of the at least one lens.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which:

FIG. 2A depicts a partial detail view of an electrosurgical device according to an embodiment.

FIG. 2B depicts a first face of a Fresnel lens according to an embodiment.

FIG. 2C depicts a second face of the Fresnel lens of FIG. 2B.

FIG. 2D depicts a first side view of the Fresnel lens of FIG. 2B.

FIG. 2E depicts another side view of the Fresnel lens of FIG. 2B.

FIG. 2F depicts another view of a face of the Fresnel lens of FIG. 2B.

FIG. 8A depicts an illumination pattern of an electrosurgical device without separation walls and in a fully extended state.

FIG. 8B depicts another illumination pattern of the electrosurgical device of FIG. 8A in a fully retracted state.

FIG. 11B depicts a further view of the electrosurgical device of FIG. 9.

FIG. 12A depicts an illumination pattern of one embodiment of an electrosurgical device comprising separation walls and in a fully extended state.

FIG. 12B depicts another illumination pattern of the electrosurgical device of FIG. 12A in a fully retracted state.

Figure 1A:
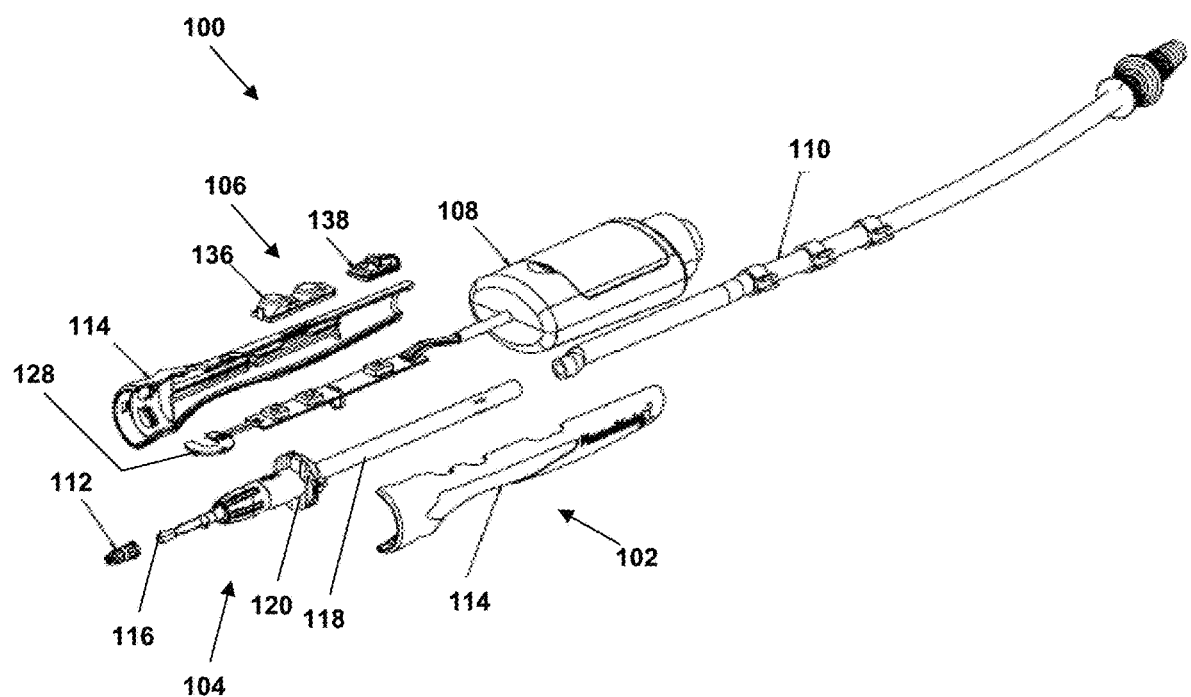
FIG. 1A depicts an exploded view of an electrosurgical device according to an embodiment.
Figure 1B:
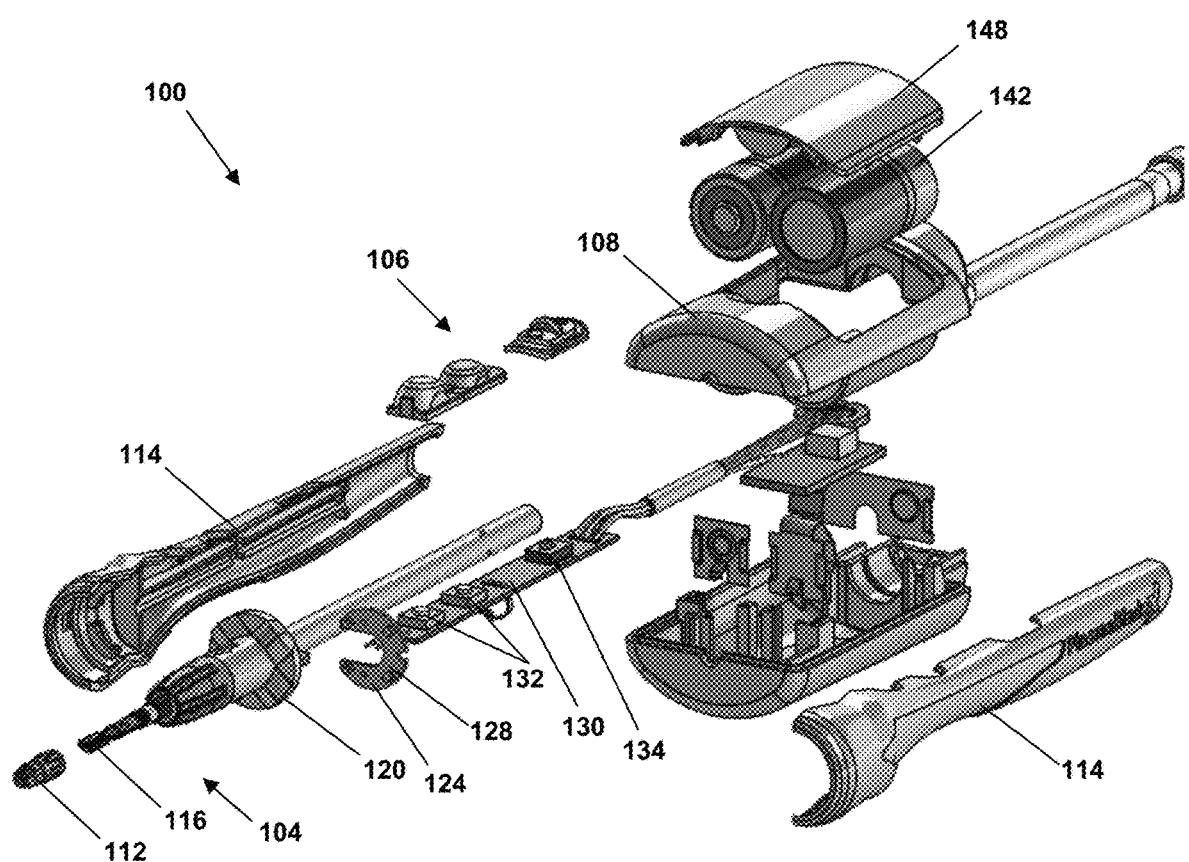
FIG. 1B depicts an exploded view of an electrosurgical device according to an embodiment.
Figure 1C:
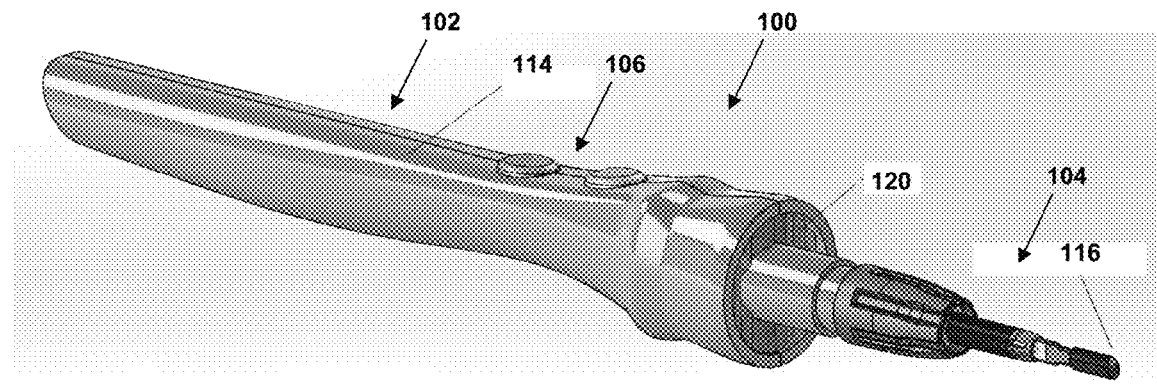
FIG. 1C depicts another view of an electrosurgical device according to an embodiment.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

Unless the context indicates otherwise, the following terms shall have the following meaning and shall be applicable both to the singular and plural:

The term "electrosurgical device" means an electrical device designed for handheld use by a surgeon to dispense RF or other energy through the tip of an electrode into target surgical tissue, in order to cut or coagulate the tissue during a surgical procedure.

The terms "radiofrequency energy" or "RF energy" mean energy from the electromagnetic spectrum having a frequency between about 3 kilohertz (3 kHz) and about 300 gigahertz (300 GHz).

The term "proximal" or "proximate," in the context of an area or end of a device or element means the operator end of the device or element, while the term "distal" means the patient end of the device or element.

Surgical devices should not unduly impede the surgeon's view of the operating field. This can be particularly troublesome in electrosurgical devices, especially those with extra features beyond energy delivery, such as added illumination, smoke evacuation, saline delivery, an extendable or rotatable shaft, a bendable tip, or other ancillary features.

In the case of an electrosurgical device that also provides added illumination (viz. light directed at the surgical field), the light desirably is emitted near the distal end of the device, where any added bulk may also directly impede the surgeon's view. Device designers have consequently sought to minimize the distal profile of such devices, and to make the associated components as small, thin and few in number as possible. At the same time, device designers have sought to meet an expressed desire of surgeons for as much light as possible provided at the point of dissection. This includes providing light in a well-defined illumination area with a crisp border and minimal or no light scatter or by providing a dispersion of light that is bright in a central area and evenly fades toward an outer diameter, because scattered or uneven light can be distracting.

Referring to FIGS. 1A, 1B, 1C, 1D and 1E, an embodiment of an electrosurgical device 100 is depicted. Generally, device 100 comprises a handpiece 102, a blade assembly 104, a switch assembly 106, a cable assembly 108, a suction tubing assembly 110, and a finger grip 112. Device 100 can comprise additional components, some of which are depicted but not particularly discussed. Other general features of electrosurgical devices like electrosurgical device 100 are described in U.S. Pat. No. 7,736,361, US 2017/0172646 and US 2016/0120592, which are incorporated herein by reference to the extent each is consistent with the instant disclosure.

Handpiece 102 comprises a housing 114, which houses blade assembly 104, switch assembly 106, and other components of device 100. Handpiece 102 provides both a comfortable handle for a user to grip during use of device 100 and a housing for blade assembly 104 and switch assembly 106. In some embodiments, handpiece 102 can be coupled to an external power source via an electrical cable (not shown in FIG. 1) or house a power source, such as one or more batteries (also not shown in FIG. 1).

Figure 1D:
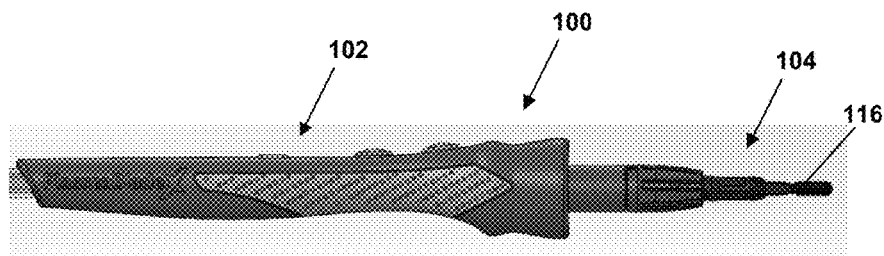
FIG. 1D depicts an electrosurgical device with a collapsed blade assembly according to an embodiment.
Figure 1E:
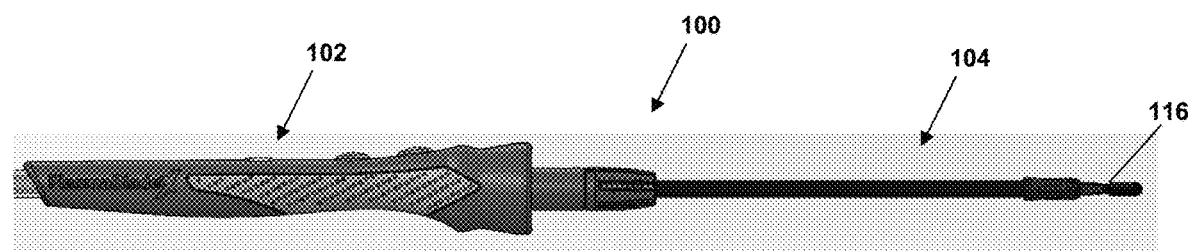
FIG. 1E depicts an electrosurgical device with an extended blade assembly according to an embodiment.

Blade assembly 104 comprises blade 116 mounted on a central shaft 118. Blade 116 also can be referred to as an electrode and, in use, can be used to cut or coagulate soft tissue of a patient. Blade 116 comprises a metal or metal alloy, such as steel, in embodiments and is coated with a dielectric material (or insulator), which focuses RF energy applied to blade 116 to achieve incisions with minimal thermal damage to the tissue. In one example, the dielectric material comprises glass. Other example dielectric materials include porcelain or ceramic, mica, plastics, and the oxides of some metals. In various embodiments, blade 116 or blade assembly 104 can telescope relative to handpiece 102 and be locked at a desired length (FIG. 1D shows blade assembly 104 in a collapsed or retracted position relative to handpiece 102, and FIG. 1E shows blade assembly 104 in an extended position relative to handpiece 102), have a bendable shaft, include suction, and comprise many different tip configurations and designs to accommodate a variety of medical procedures. The optical and illumination features discussed herein can be compatible with some or all of these variations of blade 112, providing customizability and flexibility desired by surgical users.

Referring also to FIG. 2, blade assembly 104 also comprises at least one lens element, such as ring lens 120 arranged around central shaft 118 of blade assembly 104, with a first side of ring lens 120 being adjacent to a hub portion 122 of central shaft 118 and a second side of ring lens 120 facing towards blade 116 and a distal end of device 100. In particular, ring lens 120 is arranged at a distal end of handpiece 102, centered on central shaft 118.

One embodiment of ring lens 120 is depicted in FIGS. 2A-5. In this and other embodiments, ring lens 120 can comprise a Fresnel lens, one example of which is depicted in FIGS. 2B-2F. A typical Fresnel lens has a series of facets or prisms that focus or magnify light. Some of these facets can be seen in FIGS. 2A-4, particularly in FIGS. 2B-2F. Ring lens 120 can comprise acrylic, polycarbonate, or some other transparent material. Surfaces of ring lens 120, such as the major surfaces, can be textured, for example according to texture grade MT-11006 in one embodiment. In some embodiments, ring lens 120 can comprise total internal reflection (TIR) surfaces, which can maximize the light that is first reflected within and then exited from ring lens 120. Ring lens 120 also can be considered to be a light pipe.

The lens depicted in FIGS. 2B-2F, as well as the lenses depicted in other embodiments, are only some examples of lens configurations and arrangements that can be used with embodiments of device 100. Those skilled in the art will appreciate that a lens, including a Fresnel lens, can be selected or designed according to desired light characteristics or behaviors. For example, though depicted in FIGS. 2A-5 as a single contiguous lens piece, in other embodiments ring lens 120 can comprise a plurality of individual lens elements. The individual lens elements can be coupled to or around central shaft 118 individually or together. In some embodiments (e.g., the embodiment depicted in FIGS. 6A and 6B comprising a disc 126 and apertures 127, discussed below), individual lens elements can be coupled to or with other components of device 100, such as disc 126 or apertures 127.

In device 100, any configuration of ring lens 120 can focus light from a light source (discussed herein below) on a first side of ring lens 120 and direct the light to illuminate an area around a tip of blade 116 (on the second side of ring lens 120) of blade assembly 104. The dimensions of ring lens 120 and configuration of the facets thereof can be optimized to provide a particular illumination effect. In one embodiment, ring lens 120 has a diameter of approximately 0.78 inches and is about 0.2 inches thick. Such a ring lens 120 can provide a circle of light of at least about 1.5 inches around a distal tip of blade 116 in use. In one particular example, ring lens 120 and other illumination components of device 100 provide a circle of light of about 2 inches around the distal tip of blade 116 in use. The diameter of ring lens 120 can vary from about 0.5 inches to about 1.0 inches, and the thickness of ring lens 120 can range from about 0.1 inches to about 0.25 inches. Adjusting the size or dimensions of features of ring lens 120 can provide other illumination effects, as may be desired in particular applications or uses. Dimensions can be selected such that an outer diameter of ring lens 120 does not block a user's view during use of device 100 while at the same time being large enough to provide a light angle that minimizes shadow at the tip of blade 116.

Light is provided by a light source 124. Light source 124 can comprise one or more light emitting diode (LED) light elements, incandescent light elements, or another suitable type of light element in various embodiments. Light source 124 can comprise a single light element (e.g., a single LED) or a plurality of light elements (e.g., multiple LEDs). In the embodiment depicted in FIGS. 1A-5, light source 124 comprises four LEDs. A plurality of light elements can improve the light output, such as by producing a more regular or desired illumination pattern (e.g., circular vs. oblong), while also providing increased brightness (i.e., a higher lux output). Many physician users prefer "white light," which has a typical color temperature range of 2700 Kelvin (K) to 6500 K, over warmer light with a color temperature in a range of less than 2700. The number and arrangement of the plurality of light elements also can provide thermal advantages, as spaced-apart LEDs or other light sources can benefit from improved airflow that leads to cooling. Operation of light source 124 can be controlled by switch assembly 106 such that light source 124 can be selectively turned on or off. In some embodiments, additional control of light source 124 or a characteristic thereof (e.g., direction, brightness, illumination area or size) can be controlled by switch assembly 106 or another component of device 100.

Device 100 can include additional elements and features to improve illumination effects. In one embodiment, hub portion 122 of blade assembly 104 comprises a plurality of separation walls 126. Each separation wall 126 is arranged between two adjacent LEDs of light source 124, such that adjacent ones of the pluralities of light sources 124 are separated by one of the plurality of separation walls 126. So arranged and comprising an opaque material (e.g., a plastic) or a material that reduces or eliminates light reflectance in one or more ways (e.g., via one or more of a coating, surface finish or texture, or color), separation walls 126 concentrate light from each light source 124 to a corresponding section of ring lens 120. This light concentration reduces or eliminates cross-scatter between adjacent elements of light source 124 and provides a crisper, brighter light output around the tip of blade 116.

Figure 3:
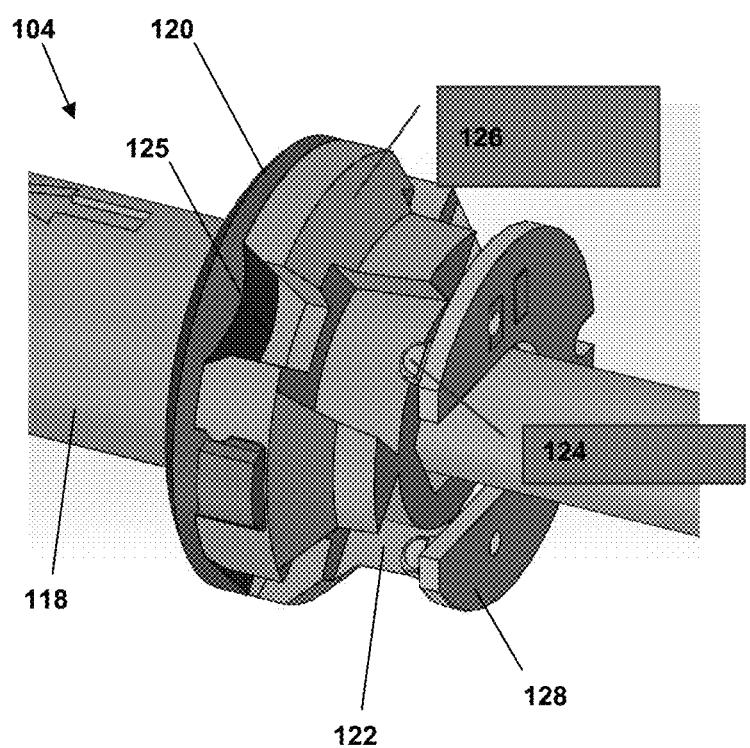
FIG. 3 depicts another view of the electrosurgical device of FIG. 2.

The configuration of one or more of ring lens 120, hub portion 122 or separation walls 126, or an interaction between two or more of these features can be selected to improve or enhance illumination provided by light source 124. Referring to FIG. 3, facets 125 of ring lens 120 are positioned between adjacent separation walls 126 and spaced apart from each light source 124 by about 0.2 inches in one example. This spacing can be larger or smaller in other embodiments and may vary according to a desired feature of one or more of the illumination system, a desired illumination effect, or device 100 overall. For example, in some embodiments a spacing between light source 124 and ring lens 120 is less than about 1.0 inches, such as less than about 0.75 inches, less than about 0.5 inches, less than about 0.33 inches, or less than about 0.25 inches. In some embodiments, the spacing between light source 124 and ring lens 120 is between about 0.15 inches and about 0.25 inches, or between about 0.15 inches and about 0.5 inches.

Figure 4:
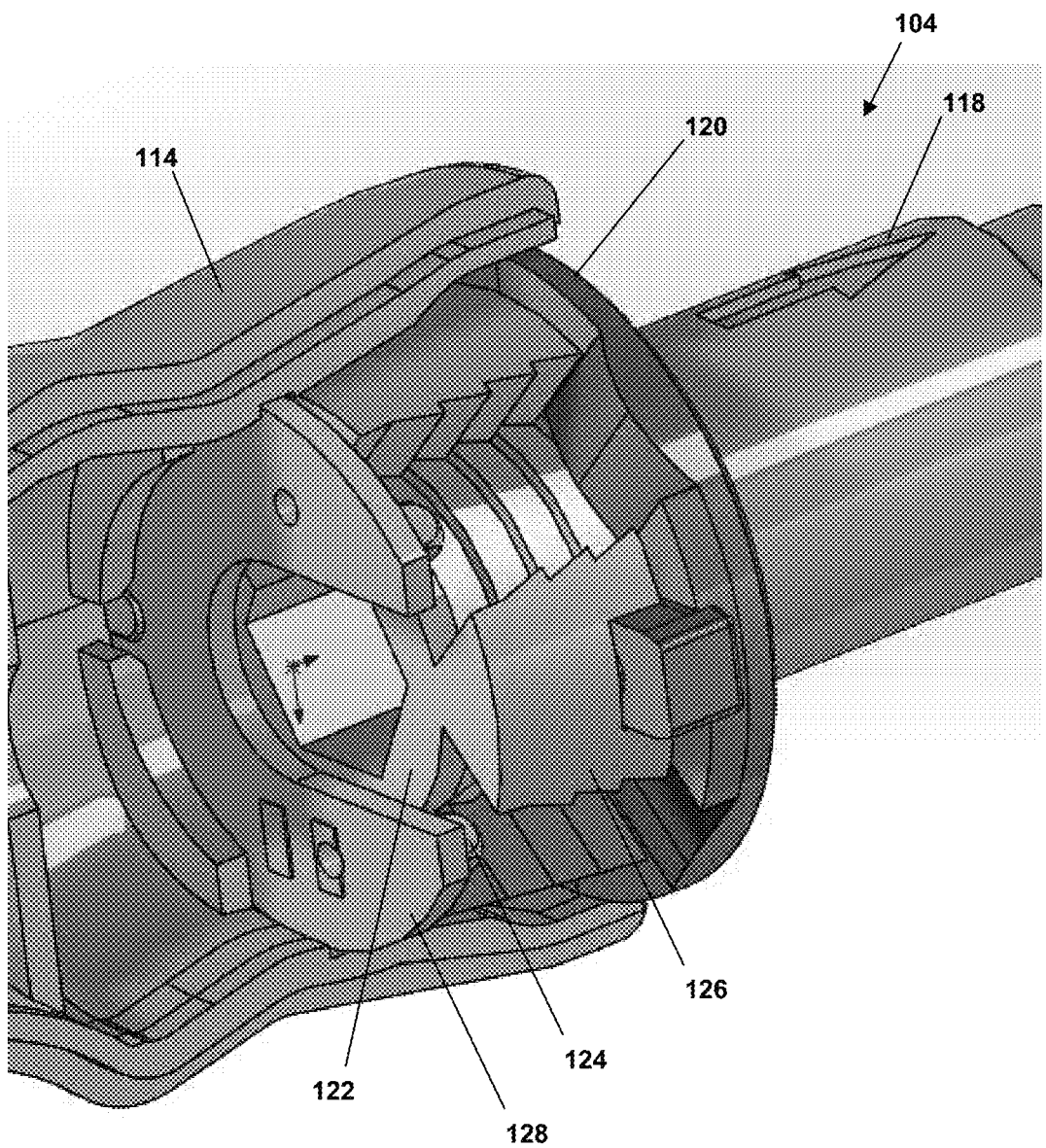
FIG. 4 depicts another embodiment of an electrosurgical device.
Figure 5:
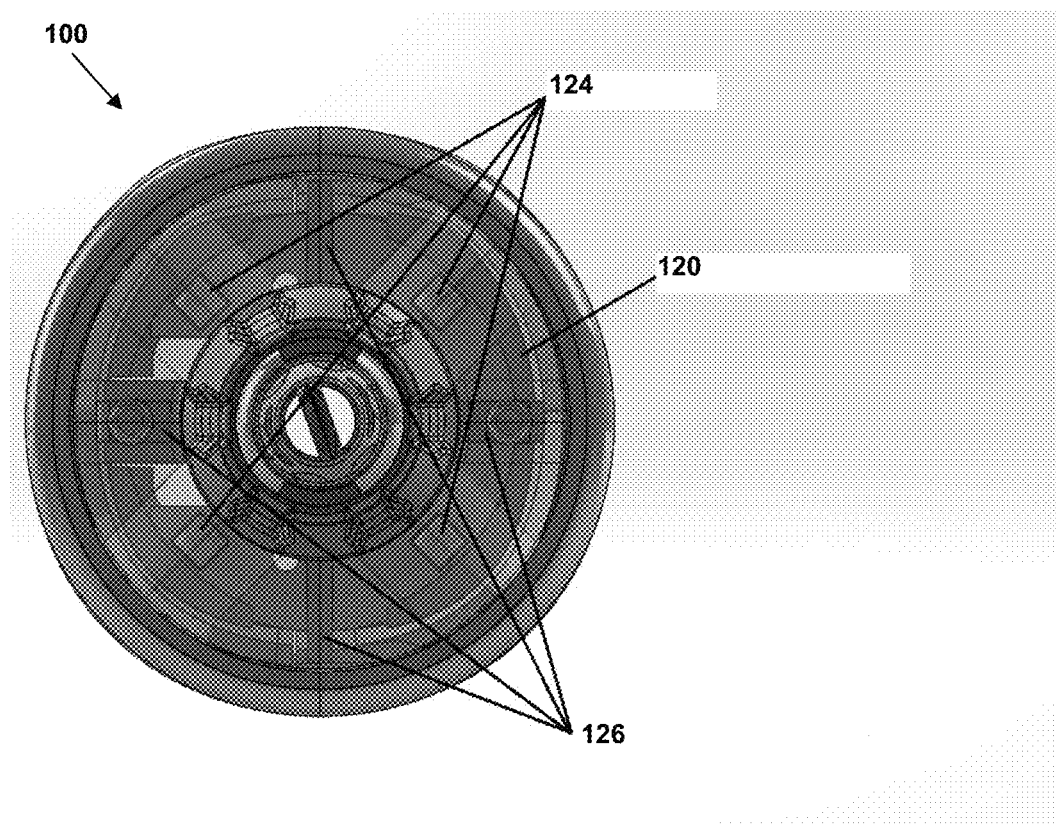
FIG. 5 depicts an end view of an electrosurgical device according to an embodiment.

In some embodiments, additional features or elements can be incorporated into the illumination system of device 100 or a component thereof in order to produce a desired illumination effect or improve a quality or characteristic of illumination. Referring to FIG. 4, surfaces of separation walls 126 or hub portion 122 can comprise a sawtooth or other angular profile, or a texture, color or other light-absorbing feature, in various embodiments. These features, or combinations of these or other features, can help direct more light to ring lens 120 and avoid light scatter.

Figure 6A:
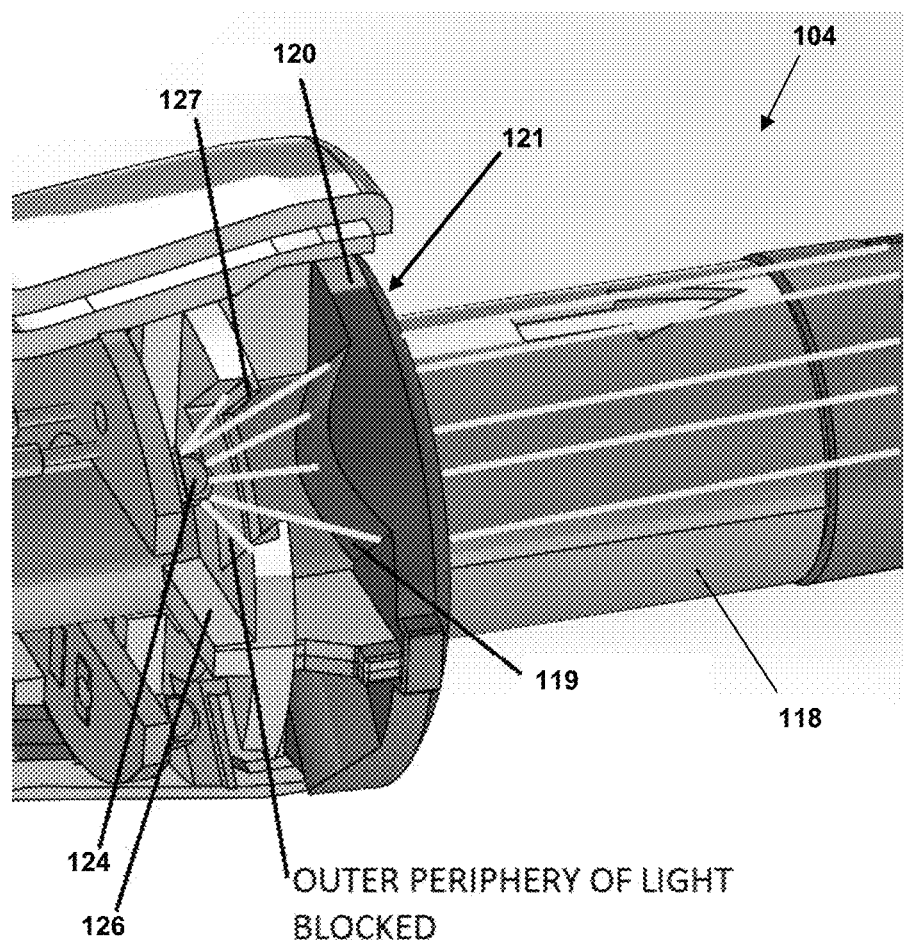
FIG. 6A depicts another embodiment of an electrosurgical device.
Figure 6B:
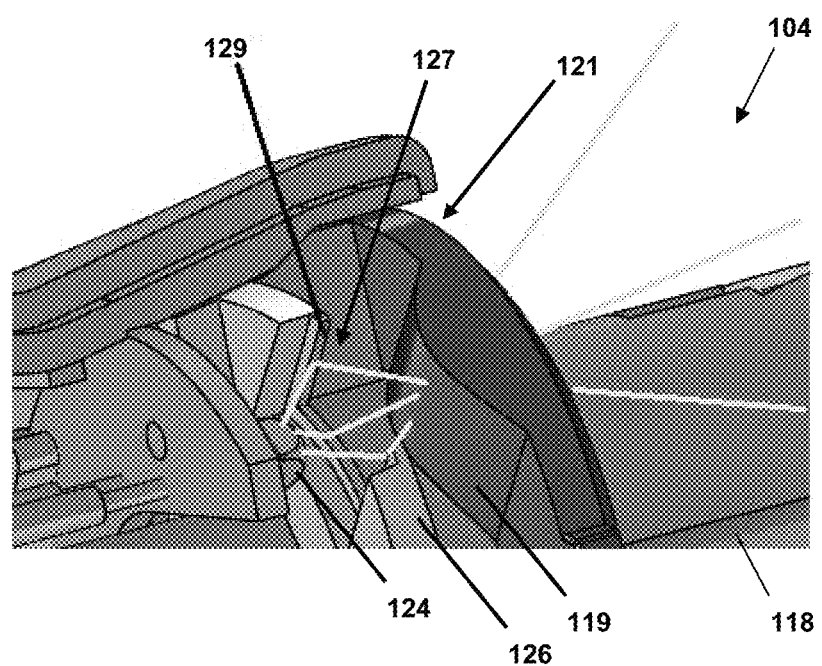
FIG. 6B depicts another view of the electrosurgical device of FIG. 6A.

Another embodiment is depicted in FIGS. 6A and 6B, in which separation walls 126 form part of a light-guiding disc 123. Disc 123 can be part of hub portion 122, distinct from hub portion 122, coupled with hub portion 122, or have some other physical arrangement relative to hub portion 122.

In addition to separation walls 126, disc 123 comprises a plurality of apertures 127. Disc 123 is positioned such that each aperture 127 is arranged between adjacent separation walls 126 on disc 123, and aligned with one light source 124 between the light source 124 and a proximal side or surface 119 of lens 120 (which can be part of a facet 125 of lens 120). Thus, in an embodiment comprising four light elements (e.g., LEDs), disc 123 can comprise four apertures 127 and four separation walls 126. In embodiments, each aperture 127 can have a width in a range of about 0.1 inches to about 0.2 inches, for example about 0.16 inches, and a height in a range of about 0.08 inches to about 0.2 inches, such as about 0.12 inches. The depth or thickness of each aperture 127 also can be adjusted, as the deeper or thicker the aperture 127 is, the more light that will be reflected, increasing the gradient of light outside of the main circle of illumination (refer, for example, to FIG. 7C and the related description below). In some embodiments, the depth of thickness of apertures 127 can be between about 0.01 inches and about 0.03 inches, such as about 0.02 inches in one embodiment. Together, apertures 127 can comprise about 25% to about 50% of the circumference of disc 123.

The arrangement and alignment of the light elements and disc 123, with separation walls 126 and apertures 127, causes light from each light source 124 to shine on the intended surface(s) of ring lens 120 (e.g., a proximal surface 119 of a facet 125 of ring lens 120) in order to produce an intended display of light at the tip of blade 116. For example, the arrangement depicted in FIGS. 6A and 6B can prevent stray light patterns from being emitted beyond a desired diameter around the tip of blade 116, which can be distracting to users (and is discussed in more detail below with respect to FIGS. 7A-8B).

In embodiments in which light source 120 comprises LEDs, it can be helpful to consider that LEDs emit light in a conical array with an included angle that can be large. For example, suitable LEDs for device 100 can shine light at an angle of about 120 degrees, and in one embodiment light from the center of each LED shines onto proximal surface 119 of ring lens 120 and emerges from a distal side or surface 121 of ring lens 120 such that it is focused to an approximate 2-inch circle at the tip of blade 116 of device 100. The size of this circle can vary as the blade assembly 104 is extended or retracted from the handpiece 102, such as between about 1 inch in diameter to about 5 inches or more in diameter. Light from the periphery of each LED, at that 120-degree angle, may reflect around, enter ring lens 120 at unintended angles or between lens surfaces, and be emitted outside the intended 2-inch diameter focus. This can result in a dark and light pattern outside the 2-inch diameter of intended illumination (see FIGS. 8A and 8B), which can be distracting to users.

Additionally, users may prefer an even gradient of dim light outside the 2-inch focus of light. This allows not only the light needed right at the point of work (e.g., at the tip of blade 116) but also some illumination to view where to work next. Apertures 127 also can provide for this low gradient of light (depicted in FIG. 7C and also discussed below). An inner edge 129 of each aperture 127 provides a reflective surface for the light. Light reflects off the bottom and both sides of edge 129 beyond the 2-inch diameter. Because edge 129 is uniform the light reflects in a fairly uniform pattern, and because edge 129 is narrow only a small amount of light is reflected, which keeps the light dim.

Figure 7A:
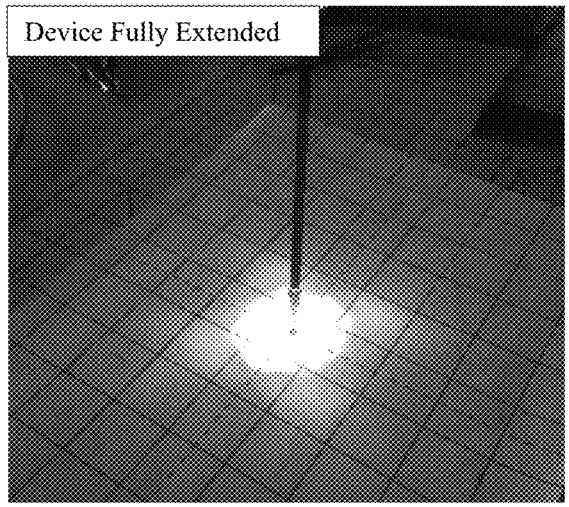
FIG. 7A depicts an illumination pattern of one embodiment of an electrosurgical device comprising separation walls and in a fully extended state.
Figure 7B:
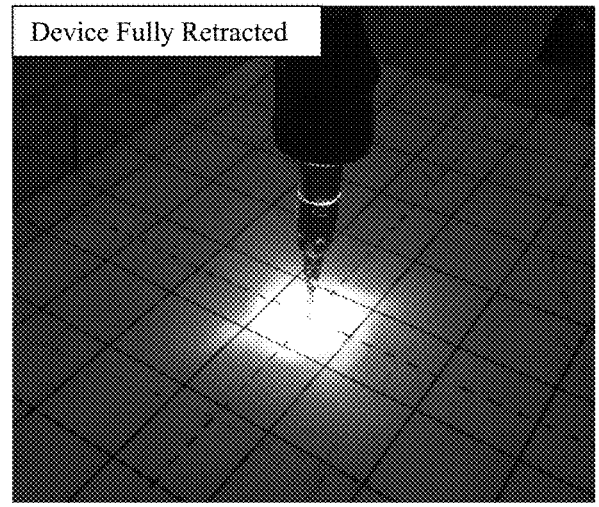
FIG. 7B depicts another illumination pattern of the electrosurgical device of FIG. 7A in a fully retracted state.

In various embodiments, one or more of these light-absorbing or light-directing features can absorb stray light that would otherwise create undesired scatter and direct light towards ring lens 120 and then the tip of blade 116. This can be seen in a comparison of FIGS. 7A, 7B and 7C with FIGS. 8A and 8B. FIG. 7A depicts device 100 (with separation walls 126) in a fully extended state (i.e., with blade assembly 104 telescoped distally), and FIG. 7B depicts device 100 (with separation walls 126) in a fully retracted state (i.e., with blade assembly 104 retracted proximally). FIG. 8A depicts device 100 (without separation walls 126) in a fully extended state (i.e., with blade assembly 104 telescoped distally), and FIG. 8B depicts device 100 (without separation walls 126) in a fully retracted state (i.e., with blade assembly 104 retracted proximally). As can be seen in FIGS. 7A and 7B, the configuration of ring lens 120, hub portion 122 and separation walls 126 cooperates with other features of device 100, such as telescoping, rotation or a bendable tip of blade assembly 104, and smoke evacuation. The ring configuration of ring lens 120 and hub portion 122 enables blade assembly 104 to telescope from a fully retracted position (in which at least a portion of blade assembly 104 is within ring lens 120 or hub portion 122) to a fully extended position.

In FIGS. 7A and 7B, a bright, crisp circle of illumination with an approximate 2-inch diameter can be seen. In FIGS. 8A and 8B, the circles of illumination are not as bright or crisp, and significant light scatter extending for many inches around the intended circle of illumination can be seen. Surgeons have reported that light scatter is distracting during use, making the illumination output of the embodiments of FIGS. 8A and 8B less desirable.

Figure 7C:
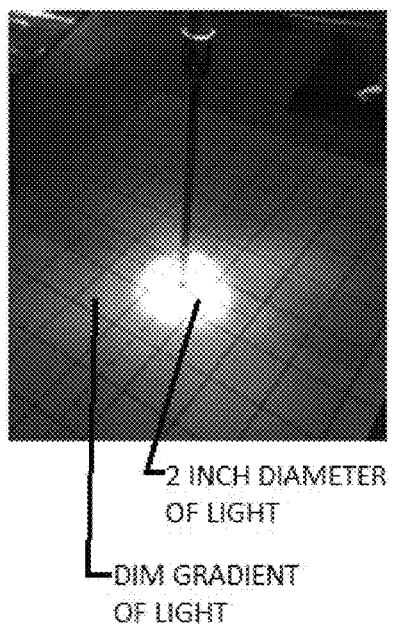
FIG. 7C depicts an illumination pattern of an embodiment of an electrosurgical device according to FIGS. 6A and 6B.
Figure 9:
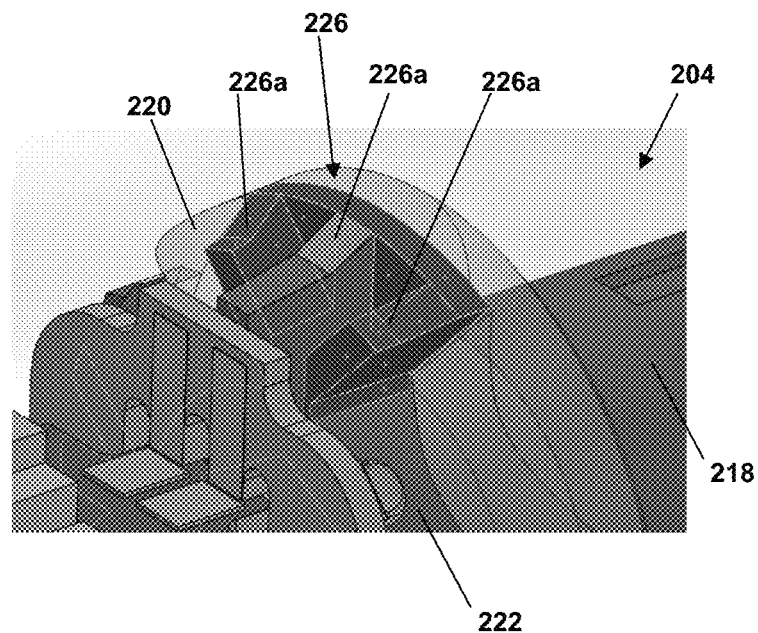
FIG. 9 depicts a partial detail view of an electrosurgical device according to an embodiment.
Figure 10A:
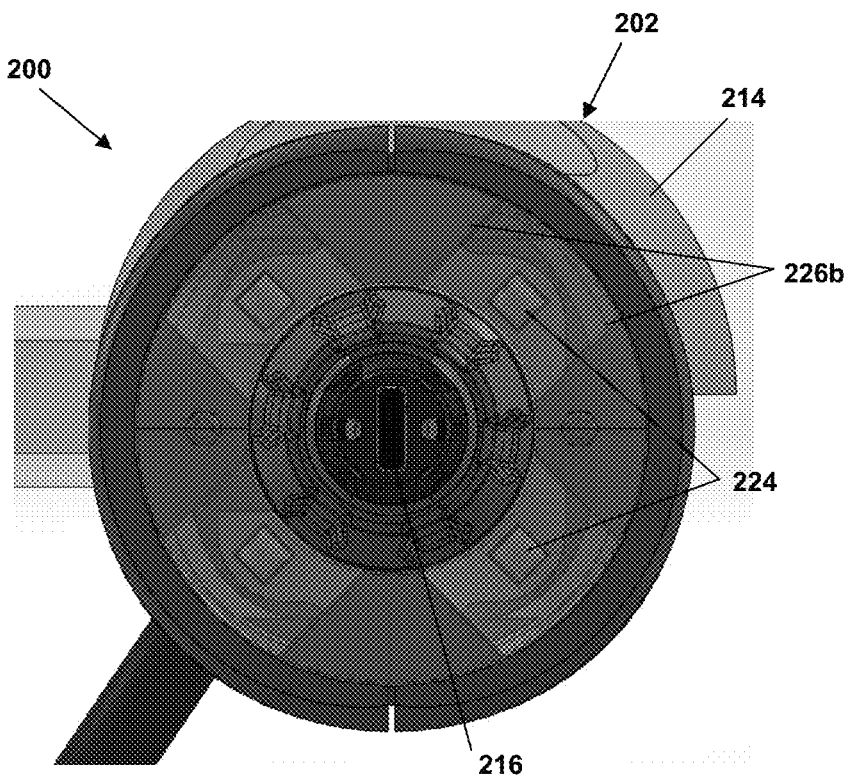
FIG. 10A depicts another view of the electrosurgical device of FIG. 9.
Figure 10B:
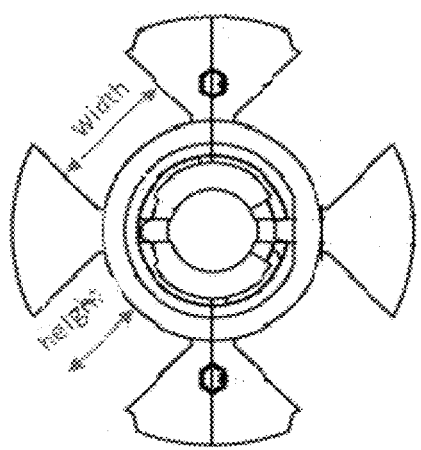
FIG. 10B depicts an annotated view of separation walls of the electrosurgical device of FIG. 9.
Figure 11A:
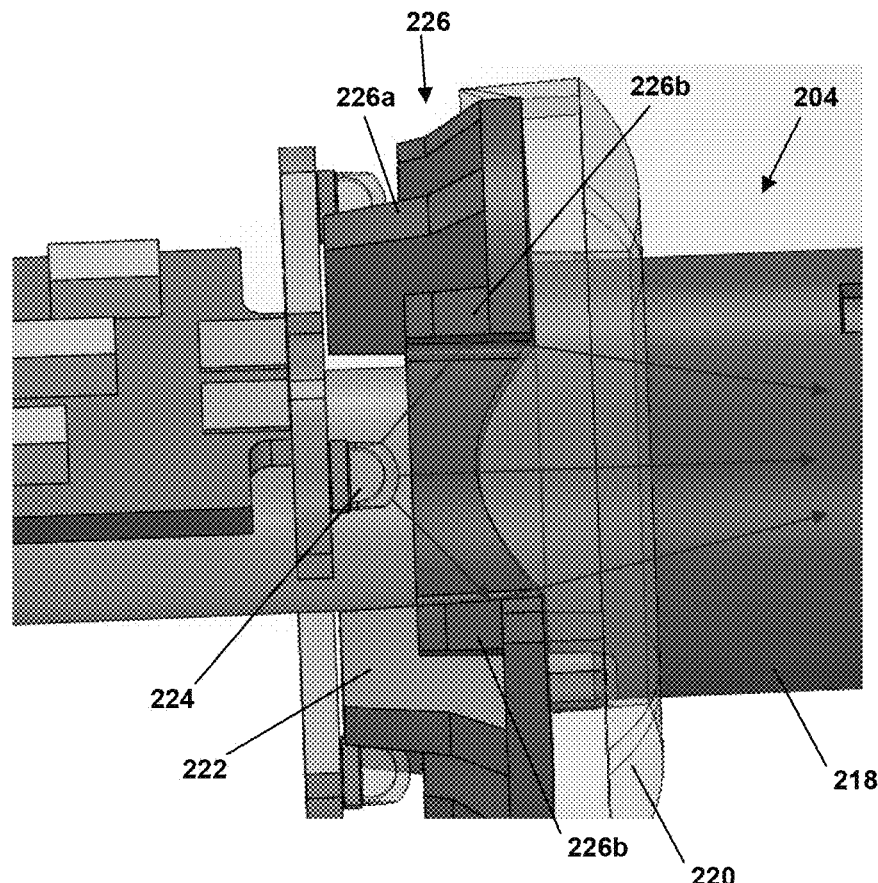
FIG. 11A depicts yet another view of the electrosurgical device of FIG. 9.

The light pattern of FIG. 7C is produced by an embodiment of device 100 that comprises apertures 127 of FIGS. 6A and 6B. FIG. 7C shows a similarly bright, crisp circle of illumination with an approximate 2-inch diameter as FIGS. 7A and 7B, and it additionally depicts a relatively even, dim gradient of light around the main circle of illumination. This gradient of light can have a diameter greater than 2 inches, such as about 3 inches or more, about 3.5 inches or more, or about 4 inches or more. In some embodiments, features of apertures 127 or other components of the embodiment of device 100 of FIGS. 6A and 6B can be selected, sized, combined or adjusted in order to tune the intensity or size of the gradient of light.

Another embodiment of a blade assembly 204 of an electrosurgical device 200 is depicted in FIGS. 9-11B. Similar features are identified by similar reference numerals, incremented by 100 (e.g., blade assembly 104 and blade assembly 204). Features of different embodiments may be similar or identical unless otherwise noted, such that like features in later embodiments may not be discussed in detail as reference may be made to similar features in previously discussed embodiments.

Similar to blade assembly 104 of FIG. 2, blade assembly 204 also comprises at least one lens element, such as ring lens 220 arranged around central shaft 218 of blade assembly 204, with a first side of ring lens 220 being adjacent to a hub portion 222 of central shaft 218 and a second side of ring lens 220 facing towards blade 216 (see FIG. 10A) and a distal end of device 100. As in other embodiments, ring lens 220 can comprise a Fresnel lens, as discussed herein above.

Light is provided by a light source 224. Light source 224 can comprise one or more LED elements, incandescent light elements, or another suitable type of light element in various embodiments. Light source 224 can comprise a single light element (e.g., a single LED) or a plurality of light elements (e.g., multiple LEDs). In the embodiment depicted in FIGS. 9-11B, light source 224 comprises four LEDs.

Hub portion 222 of blade assembly 204 further comprises a plurality of separation walls 226. As compared with the fin-like separation walls 126 depicted in FIG. 2, separation walls 226 have additional wall portions arranged between adjacent ones of light sources 224. In particular, each fin-like separation wall portion 226a is arranged between two additional separation wall portions 226b. The embodiment of FIGS. 9-11B therefore comprises four fin-like wall portions 226a and eight additional separation wall portions 226b. Each of the eight additional separation wall portions 226b are arranged more closely to each LED of light source 224 than fin-like separation wall portions 226a. In one example, and referring to FIG. 10B, adjacent separation walls are arranged such that a resulting aperture therebetween has a width of about 0.1 inches to about 0.3 inches, such as about 0.17 inches to about 0.25 inches, such as about 0.17 inches, about 0.18 inches, about 0.19 inches, about 0.20 inches, about 0.21 inches, about 0.22 inches, about 0.23 inches, about 0.24 inches, or about 0.25 inches. A height (a dimension extending outwardling from hub portion to an end of each aperture or separation wall 226) is about 0.08 inches to about 0.20 inches, such as about 0.10 inches to about 0.18 inches, such as about 0.10 inches, about 0.11 inches, about 0.12 inches, about 0.13 inches, about 0.14 inches, about 0.15 inches, about 0.16 inches, about 0.17 inches, or about 0.18 inches.

In some embodiments, fin-like separation wall portions 226a can be omitted, with only additional separation wall portions 226b provided. Still other arrangements and configurations of separation walls 226 can be implemented in other embodiments.

When arranged as depicted in FIGS. 9-11B and comprising an opaque material (e.g., a plastic) or a material that reduces or eliminates light reflectance in one or more ways (e.g., via one or more of a coating, surface finish or texture, or color), separation walls 226 concentrate light from each light source 224 to a corresponding section of ring lens 220. This can be seen in FIGS. 11A and 11B, in which arrows depict light paths from one light source 224. Light originating from the perimeter or side of light source 224 is directed towards one of the adjacent additional wall portions 226b, which redirects the light toward the central path of light originating from light source 224. Additionally, light directed toward a central axis of device 200 is redirected by a portion of hub 222; similarly, light directed away from the central axis of device 200 can be redirected toward the central light path by an interior surface of housing 214. This light concentration reduces or eliminates cross-scatter between adjacent elements of light source 224 and provides a crisper, brighter light output around the tip of blade 216.

The light concentration provided by separation walls 226 can block or redirect light in a way that further reduces the amount contributing to any light scatter, such as light contributing to a perimeter pattern, which can be distracting to physician users. Examples of undesired perimeter light patterns are depicted in FIGS. 8A and 8B. Compare these light patterns with those of FIGS. 12A and 12B, produced by an electrosurgical device comprising separation walls 226. In both extended and retracted positions of blade portion 204 of the device, the light pattern is more concentrated, with a crisper edge and a less defined pattern of any light that is scattered beyond the edge.

Figure 13:
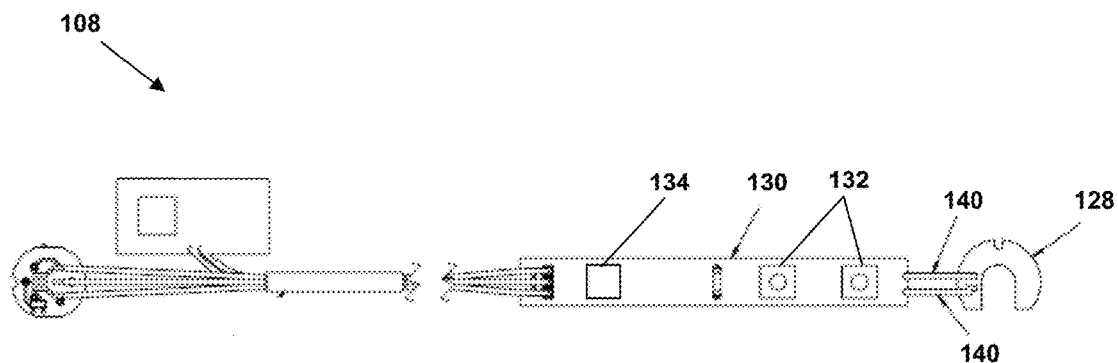
FIG. 13 depicts a cable assembly of an embodiment of an electrosurgical device.

The LEDs of light source 124 (or light source 224; for convenience, reference will be made to the embodiment of device 100, the disclosure of which also relates to the embodiment of device 200 unless otherwise stated) are arranged relative to ring lens 120 and separation walls 126 on an LED printed circuit board (PCB) 128 of cable assembly 108, which is depicted in FIGS. 1 and 13. The LEDs of light source 124 can comprise chip on board (COB) LEDs, which can comprise a plurality of LED chips. COB LEDs can take up less space and be bonded directly to a substrate, which can be LED PCB 128. LED PCB 128 can comprise a partial or full ring configuration, which can be sized and arranged such that COB LEDs mounted thereon provide light directly to ring lens 120.

LED PCB 128 is coupled to a light handle PCB 130, which includes contact switches 132 and 134 for switch assembly 106. In particular, contact switches 132 are covered by the main button pad 136 of switch assembly 106, and contact switch 134 is covered with a light switch 138 of switch assembly 106. In one embodiment, main button pad 136 covers one or more PANASONIC® EVQQ2 switches (132) by which device 100 RF electrical output can be turned on and off and otherwise controlled, and light switch 138 covers a slider switch (134) by which illumination of device 100 can be turned on and off. Other types of switches can be used in other embodiments. In another embodiment, illumination can be automatically turned on or off when device 100 is turned on or off, respectively. In still another embodiment, device 100 must first be turned on via main button pad 136 before illumination can be turned on via light switch 138. Wires 140 electrically couple LEDs of light source 124 on LED PCB 128 to light handle PCB 130 and light switch 138.

Figure 14:
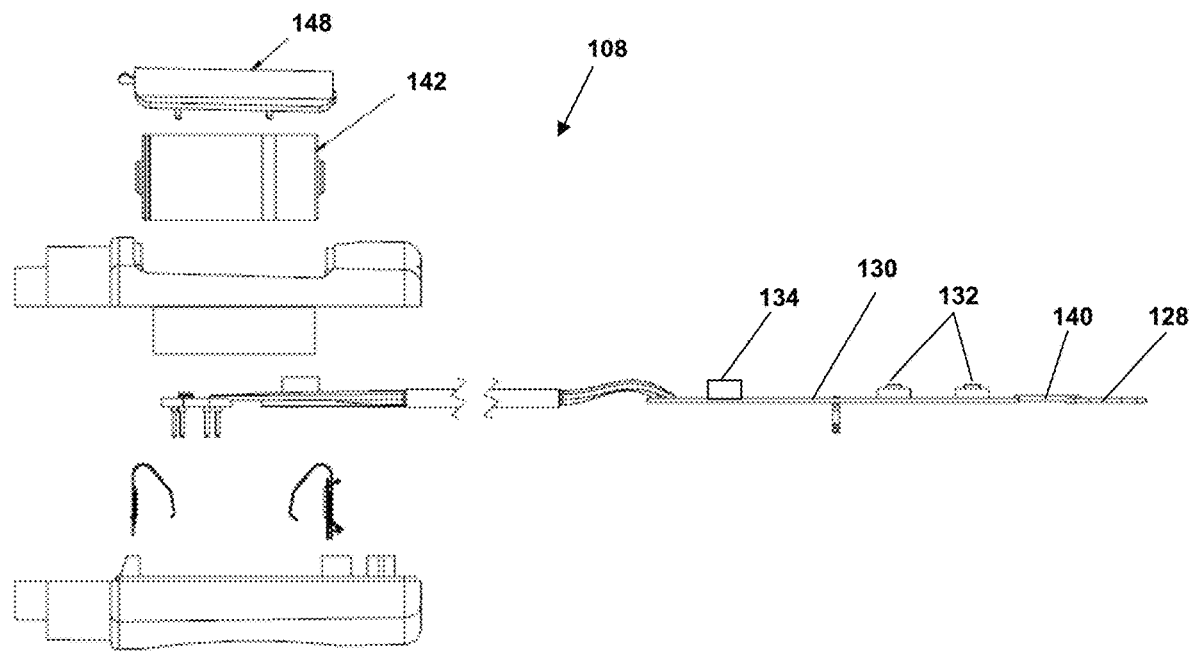
FIG. 14 depicts an exploded view of the cable assembly of the electrosurgical device of FIG. 13.

Referring also to FIG. 14, LEDs of light source 124 on LED PCB 128, or device 100 more generally, can be powered by an internal battery 142. Internal battery 142 can be disposable and replaceable, or rechargeable. In one embodiment, at least one lithium CR-123 battery is housed in cable assembly 108 and coupled to LED PCB 128 via light handle PCB 130. Battery 142 can be accessed via a battery door 148 in cable assembly 108. Batteries other than lithium or CR-123 can be used in other embodiments.

Figure 15A:
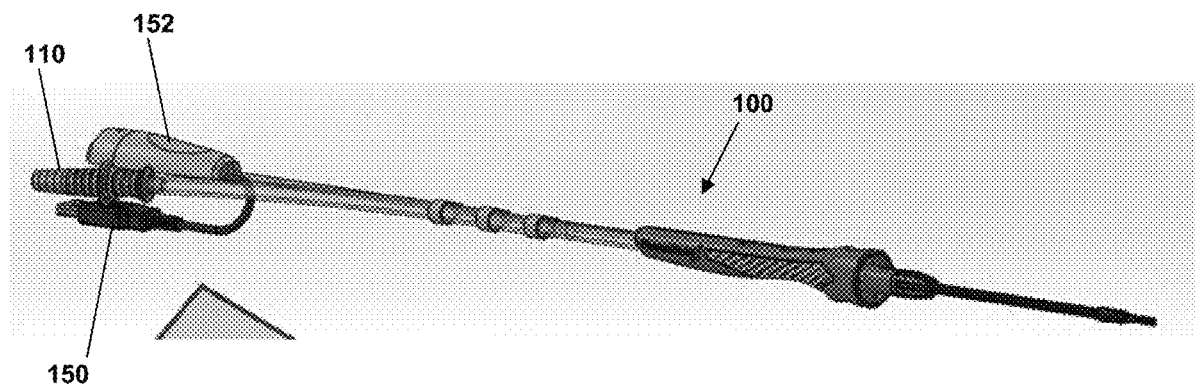
FIG. 15A depicts another embodiment of an electrosurgical device.
Figure 15B:
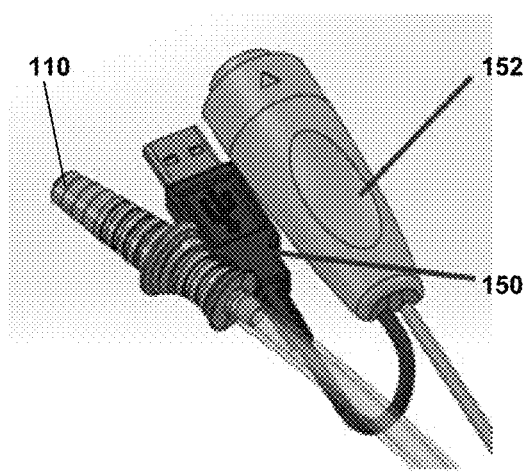
FIG. 15B depicts a connector assembly of the electrosurgical device of FIG. 15A.

In other embodiments, light source 124 or device 100 more generally can be powered by an external power source. Referring to FIGS. 15A and 15B, in some embodiments light source of device 100 is powered by a universal serial bus (USB) connector 150. USB connector 150 can be physically and electrically coupled with a generator connector 152, which (along with suction tubing assembly 110) extends from a proximal end of device 100. Generator connector 152 connects to a generator device (not depicted) to receive RF energy from the generator for device 100. At the same time, power for light source 124 can be received from the generator via connector 152 and provided to light source 124 via USB connector 150.

Various embodiments can be compatible with any current or future USB specification (e.g., USB 1.x, USB 2.x, USB 3.x). USB-compatible devices can draw either low power (typically 5 V at either 100 mA or 150 mA) or high power (typically 5 V at 500 mA or 900 mA). Some types of USB devices and connectors can support higher currents (e.g., 3 A or 5 A) and voltages (e.g., 20V). Embodiments of device 100 can be compatible with any of these or other USB devices that are developed. Still other embodiments of device 100 can use specifications and devices other than USB to power light source 124 or other components of device 100.

In various embodiments, device 100 can comprise additional components or features to provide desired illumination effects. For example, device 100 can comprise additional collimating features or lenses. In another example, light source 124 can comprise or be configured for particular light effects, such as comprising a collimator or other feature on the significant surface thereof to direct light. In yet another example, light source 124 can be arranged on LED PCB 128 or otherwise positioned in light-effective ways, such as at an angle, including orthogonally. In still another embodiment, a color or colors of LEDs of light source 124 can be selected to provide brighter or more desired light, such as white light. Light source 124 also may be arranged to user-manipulated in some embodiments, such as to be brightened or dimmed (intensity variation) or mechanically moveable, such as closer or further from the distal tip of blade 116 or relative to lens 120 in order to tune a size or other characteristic of the light directed towards the distal tip of blade 116.

Several advantages are provided by embodiments discussed herein. These include compatibility of ring lens 120, separation walls 126 and apertures 127 of the illumination system with other features of electrosurgical device 100, such as extendability and rotation, as well as a bendable tip, of blade assembly 104, and smoke evacuation. This is possible because of the ring configuration of ring lens 120, which enables other components to pass through. Thus, in some embodiments, a desired illumination effect (e.g., a relatively even circle of light around the tip of blade 116 with a diameter between about 1 inch and about 5 inches, and optionally with a dim gradient extending outside of this diameter) can be provided even when a distance between light source 124 and the tip of blade 116 varies as blade assembly 104 extends or telescopes. This distance can range in embodiments from about 2.0 inches to about 5.5 inches, such as about 2.5 inches to about 5.0 inches. During extension or telescoping of blade assembly 104, a distance between light source 124 and ring lens 120 can remain unchanged.

Additionally, separation walls 126 and 226 and apertures 127 direct light from light source 124 to ring lens 120 in a way that avoids light scatter and distracting perimeter light patterns. This can provide an additional desired illumination effect at the time of blade 116 of device 100, such as a dim gradient of illumination around the primary area of illumination.

Features and components of different embodiments discussed herein can be combined in other embodiments. In this way particular illumination effects can be designed and achieved in order to meet particular desires or needs in the industry.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. An electrosurgical device comprising:
   a central shaft;
   an electrosurgical blade coupled with the central shaft and comprising a tip;
   at least one lens element arranged around the central shaft and having a first side and a second side; and
   a plurality of light sources arranged around the central shaft to direct light to the first side of the at least one lens element;
   wherein the central shaft comprises a hub portion arranged around the central shaft and comprising a plurality of separation walls between the plurality of light sources and the first side of the at least one lens element, the plurality of separation walls spaced apart from one another around a circumference of the hub portion such that each of the plurality of light sources is between adjacent ones of the plurality of separation walls so that the adjacent ones of the plurality of separation walls guide light from the corresponding light source to the first side of the at least one lens element and therethrough toward the tip of the electrosurgical blade on the second side of the at least one lens element.

2. The electrosurgical device of claim 1, wherein the hub portion further comprises a plurality of apertures, the plurality of apertures being spaced apart from one another around the circumference of the hub portion with each of the plurality of apertures associated with a respective one of the plurality of light sources and arranged between adjacent ones of the plurality of separation walls.

3. The electrosurgical device of claim 2, wherein the plurality of light sources comprises four light-emitting diodes (LEDs), the plurality of separation walls comprises four separation walls, the plurality of apertures comprises four apertures, and the at least one lens element comprises four lens elements.

4. The electrosurgical device of claim 2, wherein each of the plurality of separation walls comprises a fin separation wall portion and two additional separation wall portions, the fin separation wall portion arranged between the two additional separation wall portions.

5. The electrosurgical device of claim 1, wherein the at least one lens element comprises a ring lens.

6. The electrosurgical device of claim 1, wherein the plurality of light sources comprises at least one (light-emitting diode) LED.

7. The electrosurgical device of claim 6, wherein the plurality of light sources comprises four LEDs and the plurality of separation walls comprises four separation walls.

8. The electrosurgical device of claim 6, wherein the at least one LED is arranged on a circuit board positioned at least partially around the central shaft.

9. The electrosurgical device of claim 6, wherein the at least one LED comprises a chip on board (COB) LED.

10. The electrosurgical device of claim 1, wherein a number of the plurality of light sources is equal to a number of the plurality of separation walls.

11. The electrosurgical device of claim 1, wherein each of the plurality of separation walls comprises a fin separation wall portion and two additional separation wall portions, the fin separation wall portion arranged between the two additional separation wall portions.

12. The electrosurgical device of claim 1, wherein the at least one lens element is a collimator total internal reflection (TIR) lens.

13. The electrosurgical device of claim 1, wherein an illuminated area around the tip of the electrosurgical blade has a diameter in a range of one inch to five inches.

14. The electrosurgical device of claim 13, wherein the illuminated area around the tip of the electrosurgical blade has a diameter of two inches.

15. The electrosurgical device of claim 1, wherein the electrosurgical blade is configured to telescope from a fully retracted position to a fully extended position.

16. The electrosurgical device of claim 15, wherein at least a portion of the electrosurgical blade is within the ring lens when the electrosurgical blade is in the fully retracted position.

17. The electrosurgical device of claim 1, wherein the plurality of light sources receive power from a source external to the electrosurgical device via a universal serial bus (USB) connector.

18. The electrosurgical device of claim 17, wherein the electrosurgical blade receives power from the source external to the electrosurgical device via another connector to which the USB connector is coupled.

19. A method comprising:
coupling an electrosurgical blade to a central shaft;
arranging at least one lens around the central shaft;
arranging a plurality of light sources around the central shaft on a first side of the at least one lens to direct light toward the first side of the at least one lens; and
forming a hub portion around the central shaft on the first side of the at least one lens such that each one of a plurality of separation walls of the hub portion, spaced apart from one another around a circumference of the hub portion, is arranged between two adjacent ones of the plurality of light sources such that each light source is guided by two adjacent separation walls.

20. The method of claim 19, further comprising forming a plurality of apertures in the hub portion, the plurality of apertures being spaced apart from one another around the circumference of the hub portion with each of the plurality of apertures associated with a respective one of the plurality of light sources and arranged between adjacent ones of the plurality of separation walls.

21. The method of claim 19, further comprising forming the electrosurgical blade to telescope from a fully retracted position to a fully extended position, wherein at least a portion of the electrosurgical blade is within the at least one lens in the fully retracted position.

22. The method of claim 19, wherein arranging at least one lens around the central shaft comprises arranging a ring lens around the central shaft.

23. The method of claim 22, further comprising forming the ring lens as a collimator total internal reflection (TIR) lens.

24. The method of claim 19, wherein arranging a plurality of light sources around the central shaft further comprises arranging a plurality of light-emitting diodes (LEDs) on a circuit board.

25. The method of claim 24, further comprising positioning the circuit board around at least a portion of the central shaft on the first side of the at least one lens.

26. The method of claim 19, further comprising causing the plurality of light sources to be illuminated such that light is guided by the plurality of separation walls to the first side of the at least one lens and therethrough to form a circle of illumination around a tip of the electrosurgical blade.

27. The method of claim 26, wherein the circle of illumination has a diameter of at least one inch.

28. The method of claim 26, wherein causing the plurality of light sources to be illuminated comprises providing power to the plurality of light sources from an external power source via a universal serial bus (USB) connector.

29. The method of claim 28, further comprising providing radio frequency (RF) power to the electrosurgical blade from the external power source via another connector to which the USB connector is coupled.

30. The method of claim 19, wherein forming the hub portion further comprises forming the plurality of separation walls to each comprise a fin separation wall portion and two additional separation wall portions, the fin separation wall portion arranged between the two additional separation wall portions.

31. An electrosurgical device comprising:
a ring lens having a circumference, a first side and a second side;
a plurality of light sources arranged on a circuit board on the first side of the ring lens, spaced apart from one another along the circumference of the ring lens; and
a plurality of separation walls each extending from the circuit board to the first side of the ring lens, the plurality of separation walls arranged such that each of the plurality of light sources is between adjacent separation walls such that the adjacent separation walls guide light from the corresponding light source to the first side of the rings lens and therethrough toward a tip of the electrosurgical device on the second side of the ring lens.

32. An electrosurgical device comprising:
a central shaft;
an electrosurgical blade coupled with the central shaft and comprising a tip;
at least one lens arranged on the central shaft and having a first side and a second side;
a plurality of light sources arranged to direct light to the first side of the at least one lens;
a plurality of separation walls each comprising a fin separation wall portion and two additional separation wall portions, the fin separation wall portion arranged between the two additional separation wall portions, the plurality of separation walls arranged around the central shaft between the plurality of light sources and the first side of the at least one lens; and
a plurality of apertures,
wherein the plurality of separation walls are spaced apart from one another around a circumference of the central shaft such that one of the plurality of light sources and one of the plurality of apertures is between adjacent ones of the plurality of separation walls so that the adjacent ones of the plurality of separation walls and a respective one of the plurality of apertures guide light from a respective one of the plurality of light sources to the first side of the at least one lens and therethrough toward the tip of the electrosurgical blade on the second side of the at least one lens.

\* \* \* \* \*